(12) United States Patent
Mao et al.

(10) Patent No.: US 9,795,581 B2
(45) Date of Patent: Oct. 24, 2017

(54) CRYSTALLINE FORMS OF (N,N-DIETHYLCARBAMOYL)METHYL METHYL (2E)BUT-2-ENE-1,4-DIOATE, METHODS OF SYNTHESIS AND USE

(71) Applicant: XENOPORT, Inc., Redwood City, CA (US)

(72) Inventors: Chen Mao, Foster City, CA (US); Randall A. Scheuerman, Santa Clara, CA (US); Sami Karaborni, Cupertino, CA (US)

(73) Assignee: XENOPORT, INC., Redwood City, CA (US)

( * ) Notice: Subject to any disclaimer, the term of this patent is extended or adjusted under 35 U.S.C. 154(b) by 0 days.

(21) Appl. No.: 15/589,087

(22) Filed: May 8, 2017

(65) Prior Publication Data

US 2017/0239206 A1 Aug. 24, 2017

Related U.S. Application Data

(63) Continuation of application No. 15/214,563, filed on Jul. 20, 2016, now Pat. No. 9,682,057, which is a continuation of application No. 14/478,627, filed on Sep. 5, 2014, now Pat. No. 9,416,096.

(60) Provisional application No. 61/874,758, filed on Sep. 6, 2013.

(51) Int. Cl.
*C07C 235/06* (2006.01)
*A61K 31/225* (2006.01)
*A61K 9/00* (2006.01)

(52) U.S. Cl.
CPC .......... *A61K 31/225* (2013.01); *A61K 9/0053* (2013.01)

(58) Field of Classification Search
None
See application file for complete search history.

*Primary Examiner* — Timothy R Rozof
(74) *Attorney, Agent, or Firm* — King & Spalding

(57) ABSTRACT

Disclosed herein are crystalline forms of (N,N-Diethylcarbamoyl)methyl methyl (2E)but-2-ene-1,4-dioate, which is a prodrug of methyl hydrogen fumarate. Crystalline form 1, Crystalline form 2, Crystalline 3, and Crystalline form 4 are disclosed.

14 Claims, 12 Drawing Sheets

CRYSTALLINE FORMS OF (N,N-DIETHYLCARBAMOYL)METHYL METHYL (2E)BUT-2-ENE-1,4-DIOATE, METHODS OF SYNTHESIS AND USE

CROSS-REFERENCE

The application is a continuation of U.S. patent application Ser. No. 15/214,563, filed Jul. 20, 2016, which is a continuation of U.S. patent application Ser. No. 14/478,627, filed Sep. 5, 2014, which claims the benefit of priority to U.S. Provisional Patent Application No. 61/874,758, filed Sep. 6, 2013. The complete disclosure of each of the above-identified applications is fully incorporated herein by reference.

FIELD

Disclosed herein are novel crystalline forms of (N,N-Diethylcarbamoyl)methyl methyl (2E)but-2-ene-1,4-dioate.

BACKGROUND

In general, crystalline forms of drugs are utilized in dosage forms rather than amorphous forms of drugs, in part, because of their superior stability. For example, in many situations, an amorphous drug converts to a crystalline drug form upon storage. Because amorphous and crystalline forms of a drug typically have different physical properties, chemical properties, potencies and/or bioavailabilities, such interconversion is undesirable for safety reasons in pharmaceutical administration.

Polymorphs are crystals of the same molecule which have different physical properties because the crystal lattice contains a different arrangement of molecules. For example, certain polymorphs can include different hydration states that incorporate water into the crystalline structure without chemical alteration of the molecule itself. In that regard, certain compounds can exist in anhydrous and hydrated forms, where the hydrated forms can include, for example, hydrates, dihydrates, trihydrates, and the like, or partial hydrates such as hemihydrates. The different physical properties exhibited by polymorphs can affect important pharmaceutical parameters such as storage, stability, compressibility, density (which is important in formulation and product manufacturing) and dissolution rates (which are important in determining bioavailability). Stability differences may result from changes in chemical reactivity (e.g., differential hydrolysis or oxidation, such that a dosage form discolors more rapidly when the dosage form comprises one polymorph rather than another polymorph), mechanical changes (e.g., tablets crumble on storage as a kinetically favored crystalline form converts to a thermodynamically more stable crystalline form) or both (e.g., tablets of one polymorph are more susceptible to breakdown at high humidity). Solubility differences between polymorphs may, in extreme situations, result in transitions to crystalline forms that lack potency and/or are toxic. In addition, the physical properties of a particular crystalline form may be important in pharmaceutical processing. For example, one particular crystalline form may form solvates more readily or may be more difficult to filter and wash free of impurities than other forms (e.g., particle shape and size distribution might be different between one crystalline form relative to other forms).

Regulatory agencies such as the United States Food and Drug Administration closely regulate the polymorphic content of the active component of a drug in solid dosage forms. In general, regulatory agencies require batch-by-batch monitoring for polymorphic drugs if anything other than the pure, thermodynamically preferred polymorph is marketed. Accordingly, medical and commercial reasons favor synthesizing and marketing the most thermodynamically stable polymorph of a crystalline drug substance in solid drugs, which is substantially free of other, less favored polymorphs.

(N,N-Diethylcarbamoyl)methyl methyl (2E)but-2-ene-1,4-dioate (1) has the following chemical structure:

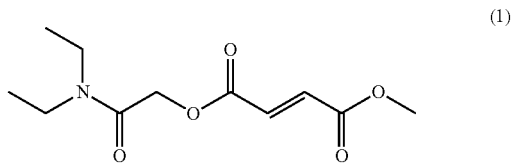 [SMILES: CCN(CC)C(=O)COC(=O)/C=C/C(=O)OC]

(1)

Compound (1) is a prodrug of methyl hydrogen fumarate. Once administered, the compound is metabolized in vivo into an active metabolite, namely, methyl hydrogen fumarate (MHF) which is also referred to herein as monomethyl fumarate (MMF). The in vivo metabolism of (N,N-Diethylcarbamoyl)methyl methyl (2E)but-2-ene-1,4-dioate to MHF/MMF is illustrated below:

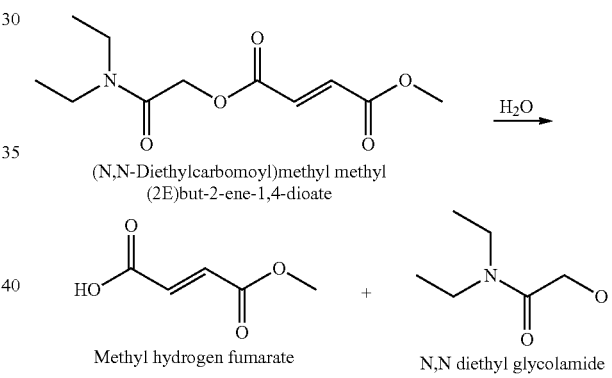

Compound (1) is synthesized in Example 1 of Gangakhedkar et al. U.S. Pat. No. 8,148,414 and is disclosed as having a melting point between 53° C. and 56° C. Oral dosage forms comprising compound (1) are disclosed in U.S. patent application Ser. No. 13/973,456 filed Aug. 22, 2013, and Ser. No. 13/973,622 filed Aug. 22, 2013. High drug load formulations of compound (1) are disclosed in U.S. patent application Ser. No. 13/973,542 filed Aug. 22, 2013. Therapeutic uses and methods of treatment for compound (1) are disclosed in U.S. patent application Ser. No. 13/973,820 filed Aug. 22, 2013, Ser. No. 13/906,155 filed May 30, 2013, Ser. No. 13/973,700 filed Aug. 22, 2013, and Ser. No. 13/973,780 Aug. 22, 2013. Methods of making compound (1) are disclosed in U.S. patent application Ser. No. 14/298,713 filed Jun. 6, 2014. The contents of each of the above referenced patents and patent applications are hereby incorporated by reference in their entireties.

Co-crystalline forms of (N,N-Diethylcarbamoyl)methyl methyl (2E)but-2-ene-1,4-dioate with different co-formers are disclosed in U.S. patent application Ser. No. 14/072,138 filed Nov. 5, 2013, the contents of which is hereby incorporated by reference in its entirety.

SUMMARY

The present disclosure describes novel crystalline forms of (N,N-Diethylcarbamoyl)methyl methyl (2E)but-2-ene-1,4-dioate having improved physicochemical properties that may be used in pharmaceutical processing and in pharmaceutical compositions and therapeutic methods of treatment.

In a first aspect, a crystalline form 1 of (N,N-Diethylcarbamoyl)methyl methyl (2E)but-2-ene-1,4-dioate, pharmaceutical compositions comprising the form 1, and methods of administering the form 1 to a patient in need thereof for treating a disease, are provided.

In a second aspect, a crystalline form 2 of (N,N-Diethylcarbamoyl)methyl methyl (2E)but-2-ene-1,4-dioate, pharmaceutical compositions comprising the form 2, and methods of administering the form 2 to a patient in need thereof for treating a disease, are provided.

In a third aspect, a crystalline form 3 of (N,N-Diethylcarbamoyl)methyl methyl (2E)but-2-ene-1,4-dioate, pharmaceutical compositions comprising the form 3, and methods of administering the form 3 to a patient in need thereof for treating a disease, are provided.

In a fourth aspect, a crystalline form 4 of (N,N-Diethylcarbamoyl)methyl methyl (2E)but-2-ene-1,4-dioate, pharmaceutical compositions comprising the form 4, and methods of administering the form 4 to a patient in need thereof for treating a disease, are provided.

DEFINITIONS

Figure 1:
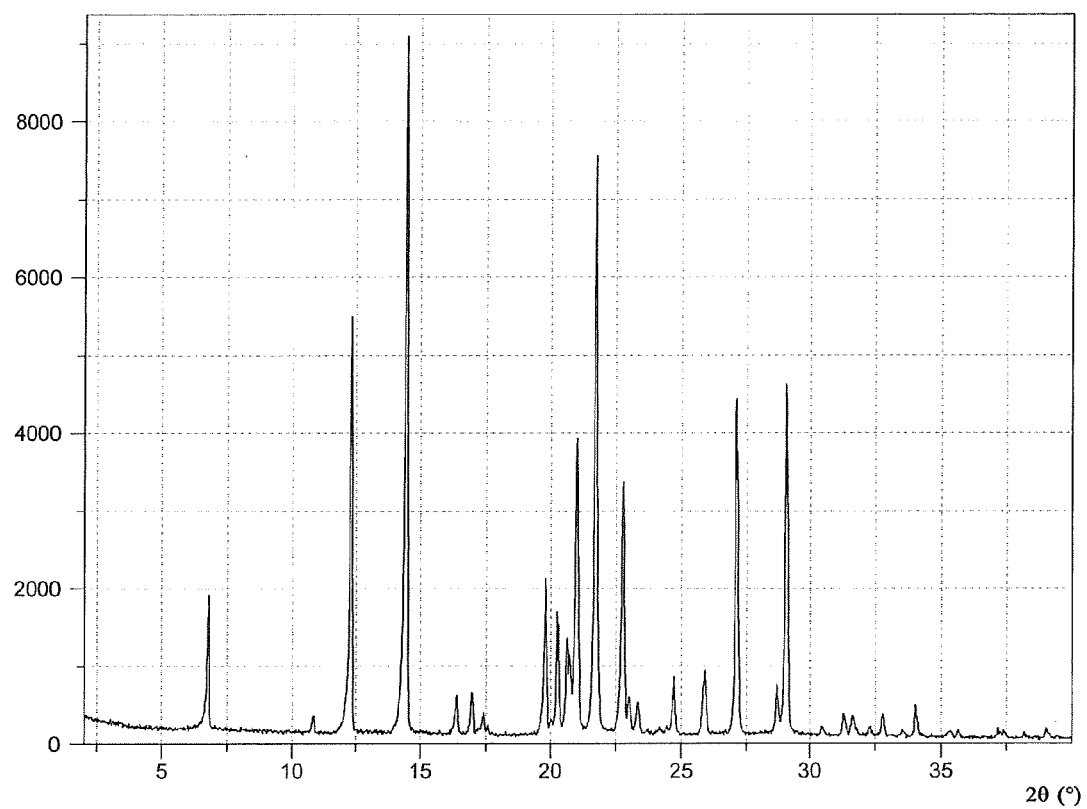
FIG. 1 is an X-ray powder diffractogram (XRPD) of a crystalline form 1 of (N,N-Diethylcarbamoyl)methyl methyl (2E)but-2-ene-1,4-dioate.

Unless defined otherwise, all technical and scientific terms used herein have the same meaning as is commonly understood by one of skill in the art to which the present disclosure belongs.

"Bioavailability" refers to the amount of a drug that reaches the systemic circulation of a patient following administration of the drug, or a prodrug thereof, to the patient and may be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or prodrug thereof to the patient, and $T_{max}$ is the time to the maximum concentration ($C_{max}$) of a drug in the plasma or blood of a patient following administration of a dose of the drug or prodrug thereof to the patient.

"Crystalline" means having a regularly repeating arrangement of molecules.

"Crystalline (N,N-Diethylcarbamoyl)methyl methyl (2E)but-2-ene-1,4-dioate" refers to a compound in which crystalline (N,N-Diethylcarbamoyl)methyl methyl (2E)but-2-ene-1,4-dioate is not associated with water molecules. Other chemical names for crystalline (N,N-Diethylcarbamoyl)methyl methyl (2E)but-2-ene-1,4-dioate include, without limitation, anhydrous crystalline (N,N-Diethylcarbamoyl)methyl methyl (2E)but-2-ene-1,4-dioate, crystalline polymorphic forms of (N,N-Diethylcarbamoyl)methyl methyl (2E)but-2-ene-1,4-dioate, crystalline forms and anhydrous crystalline polymorphic forms of (N,N-Diethylcarbamoyl)methyl methyl (2E)but-2-ene-1,4-dioate.

"Disease" refers to a disease, disorder, condition, symptom, or indication. This term is used interchangeably with the phrase "disease or disorder."

"Dosage form" refers to a form of a formulation that comprises an amount of active agent or a prodrug of an active agent, for example, the monomethyl fumarate prodrug (N,N-Diethylcarbamoyl)methyl methyl (2E)but-2-ene-1,4-dioate, which can be administered to a patient to achieve a therapeutic effect. An oral dosage form is intended to be administered to a patient via the mouth and swallowed. Examples of oral dosage forms include capsules, tablets, and liquid suspensions. A dose of a drug may include one or more dosage forms administered simultaneously or over a period of time.

"Patient" includes mammals, such as for example, humans.

"Pharmaceutical composition" refers to a composition comprising at least one compound provided by the present disclosure and at least one pharmaceutically acceptable vehicle with which the compound is administered to a patient.

"Pharmaceutically acceptable" refers to approved or approvable by a regulatory agency of a federal or a state government, listed in the U.S. Pharmacopeia, or listed in other generally recognized pharmacopeia for use in mammals, including humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing, with which crystalline forms of (N,N-Diethylcarbamoyl)methyl methyl (2E)but-2-ene-1,4-dioate can be administered to a patient, which does not destroy the pharmacological activity thereof, and which is nontoxic when administered in doses sufficient to provide a therapeutically effective amount of one or both of the compounds.

"Prodrug" refers to a derivative of an active compound (such as a drug) that undergoes a transformation under the conditions of use, such as within the body, to release the active compound or drug. Prodrugs are frequently, but not necessarily, pharmacologically inactive until converted into the active compound or drug. Prodrugs can be obtained by bonding a promoiety (defined herein), typically via a functional group, to a drug. For example, the monomethyl fumarate prodrug (N,N-Diethylcarbamoyl)methyl methyl (2E)but-2-ene-1,4-dioate is metabolized within a patient's body to form the parent drug monomethyl fumarate.

"Promoiety" refers to a group bonded to a drug, typically to a functional group of the drug, via one or more bonds that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach, or the agent may be supplied exogenously. For example, the promoiety of (N,N-Diethylcarbamoyl)methyl methyl (2E)but-2-ene-1,4-dioate is:

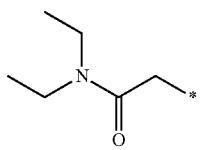 [SMILES: *CC(=O)N(CC)CC]

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; the rate of excretion of a disclosed crystalline form; the duration of the treatment; any drugs used in combination or coincidental with the specific compound employed; the discretion of the prescribing physician; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001. A therapeutically effective amount in any given instance can be readily ascertained by those skilled in the art and/or is capable of determination by routine experimentation.

The term "purity", when referring to one of the crystalline forms 1, 2, 3 and/or 4 of (N,N-Diethylcarbamoyl)methyl methyl (2E)but-2-ene-1,4-dioate disclosed herein, means the degree to which the particular crystalline form is undiluted or unmixed with another crystalline form and/or extraneous material(s), and is expressed as a percentage by weight (wt %). The term "purity", when referring to a formulation or dosage form of one of the crystalline forms 1, 2, 3 and/or 4 of (N,N-Diethylcarbamoyl)methyl methyl (2E)but-2-ene-1,4-dioate disclosed herein, which formulation or dosage form comprises the particular crystalline form as the active pharmaceutical agent (as well as one or more other materials such as a pharmaceutically acceptable vehicle), means the degree to which the active pharmaceutical agent in the formulation or dosage form comprises that particular crystalline form and no other crystalline form(s) of (N,N-Diethylcarbamoyl)methyl methyl (2E)but-2-ene-1,4-dioate, and is also expressed as a percentage by weight (wt %). Since the weight percent of a particular crystalline form can vary with measurements taken by different instruments, different calibrations and/or different software packages, those skilled in the art will appreciate that any measured purity level will show some variability. Due to these sources of variability, it is common to recite purity using the word "about" or "at least" when referring to the percent purity of a crystalline form.

"Treating" or "treatment" of any disease or disorder refers to reversing, alleviating, arresting or ameliorating a disease or disorder, or at least one of the clinical symptoms of a disease or disorder, reducing the risk of acquiring at least one of the clinical symptoms of a disease or disorder, inhibiting the progress of a disease or disorder or at least one of the clinical symptoms of the disease or disorder, or reducing the risk of developing at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to protecting against or delaying the onset of at least one or more symptoms of a disease or disorder in a patient.

Reference is now made in detail to certain embodiments of crystalline forms, dosage forms and methods of use. The disclosed embodiments are not intended to be limiting of the claims. To the contrary, the claims are intended to cover all alternatives, modifications, and equivalents.

DETAILED DESCRIPTION

The present disclosure is directed to crystalline forms of (N,N-Diethylcarbamoyl)methyl methyl (2E)but-2-ene-1,4-dioate.

Four different crystalline forms of (N,N-Diethylcarbamoyl)methyl methyl (2E)but-2-ene-1,4-dioate are disclosed herein. The first form is form 1. The second form is form 2. The third form is form 3. The fourth form is form 4.

TABLE 1

| Crystalline Forms | Melting Point (° C.) |
|---|---|
| Form 1 | 58 |
| Form 2 | 50 |
| Form 3 | 47 |
| Form 4 | Unknown |

As can be seen from the data in Table 1, the form 1, form 2, and form 3 disclosed herein each exhibit a different melting point from each other.

Differential scanning calorimetry, or DSC, is a thermoanalytical technique in which the difference in the amount of heat required to increase the temperature of a sample and reference is measured as a function of temperature. DSC data shows differential heat flow plotted against temperature. As a sample undergoes a thermal event, it is effectively altering the heat flow due to the latent heat associated with the thermal event, which is then reflected as a peak or a shift in baseline. DSC can be used to characterize thermal properties of crystalline forms, such as melting temperature or heat of fusion. Therefore, the melting points of the crystalline form 1, form 2 and form 3 disclosed herein can be characterized by DSC. The crystalline form 4 can be characterized by having a DSC thermogram peak.

Single-crystal X-ray diffraction provides three-dimensional structural information about the positions of atoms and bonds in a crystalline form. It is not always possible or feasible, however, to obtain such a structure from a crystalline form due to, for example, insufficient crystal size or difficulty in preparing crystals of sufficient quality for single-crystal X-ray diffraction. Structural identification information can, however, be obtained from other solid-state techniques such as X-ray powder diffraction and Raman spectroscopy. These techniques are used to generate data on a solid crystalline form. Once that data has been collected on a known crystalline form, that data can be used to identify the presence of that crystalline form in other materials. Thus, these data effectively characterize the crystalline form. For example, an X-ray powder diffraction pattern, or a portion thereof, can serve as a fingerprint which characterizes a crystalline form.

An X-ray powder diffraction plot is an x-y graph with scattering angles 2θ (diffraction) on the x-axis and intensity on the y-axis. The peaks within this plot can be used to characterize a crystalline form. Although the peaks within an entire diffractogram can be used to characterize a crystalline form, a subset of the more characteristic peaks can also be used to accurately characterize a crystalline form. The data is often represented by the position of the peaks on the x-axis rather than the intensity of peaks on the y-axis because peak intensity may vary with sample orientation. There is also variability in the position of peaks on the x-axis. There are several sources of this variability, one of which comes from sample preparation. Samples of the same crystalline material prepared under different conditions may yield slightly different diffractograms. Factors such as particle size, moisture content, solvent content, and orientation can affect how a sample diffracts X-rays. Another source of variability comes from instrument parameters. Different X-ray instruments operate using different parameters and these may lead to slightly different diffraction patterns from the same crystalline form. Likewise, different software packages process X-ray data differently and this also leads to variability. These and other sources of variability are known to those of ordinary skill in the art. Due to these sources of variability, it is common to recite X-ray diffraction peaks using the word "about" prior to the peak value in 2θ. The word "about" incorporates this variability which under most sampling conditions, and most data collection and data processing conditions, leads to a variability in peak position of about plus or minus 0.2 scattering angle (2θ). Thus, when a peak is said to be at about 10.5 scattering angle (2θ), under most sampling, data collection, and data processing conditions, that peak will appear anywhere between 10.3 (2θ) and 10.7 (2θ). In characterizing the crystalline forms disclosed herein, the X-ray diffraction peaks were all measured using Cu—K$_\alpha$ radiation and all peaks herein cited refer to peaks diffracted from X-rays with that wavelength.

High-performance liquid chromatography, or HPLC, is a chromatographic technique used to separate the compounds in a mixture, to identify each compound, and to quantify each compound. HPLC is a technique known in the art to determine the purity of a compound. The purity of forms 1, 2, 3 and 4 of (N,N-Diethylcarbamoyl)methyl methyl (2E)but-2-ene-1,4-dioate can be determined using HPLC as is well known to those of ordinary skill in the art.

(N,N-Diethylcarbamoyl)methyl methyl (2E)but-2-ene-1,4-dioate: Form 1

One crystalline form disclosed herein is form 1 of (N,N-Diethylcarbamoyl)methyl methyl (2E)but-2-ene-1,4-dioate. Differential scanning calorimetry (DSC) analysis of form 1 shows a melting point between about 56° C. and about 60° C., in certain embodiments between about 57° C. and about 59° C., and in certain embodiments at about 58° C.

The purity of crystalline form 1 of (N,N-Diethylcarbamoyl)methyl methyl (2E)but-2-ene-1,4-dioate is at least 99 wt % as measured by HPLC. In certain embodiments the purity of crystalline form 1 is at least 99.5 wt % as measured by HPLC. In certain embodiments the purity of crystalline form 1 is at least 99.9 wt % as measured by HPLC.

FIG. 1 is an X-ray powder diffractogram (XRPD) of form 1 of the (N,N-Diethylcarbamoyl)methyl methyl (2E)but-2-ene-1,4-dioate showing the diffraction pattern measured using Cu—K$_\alpha$ radiation. Table 2 lists the approximate numerical values of the XRPD peak positions of the FIG. 1 diffractogram.

TABLE 2

XRPD Peaks for (N,N-Diethylcarbamoyl)methyl methyl (2E)but-2-ene-1,4-dioate: Form 1

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 14.4566 | 8669.85 | 0.0836 | 6.12715 | 100 |
| 21.7146 | 6282.16 | 0.1004 | 4.09281 | 72.46 |
| 12.335 | 5063.34 | 0.1004 | 7.17583 | 58.4 |
| 29.0316 | 4396.74 | 0.0836 | 3.07579 | 50.71 |
| 27.0823 | 4235.59 | 0.0836 | 3.29258 | 48.85 |
| Peaks (All) | | | | |
| 6.7857 | 1705.57 | 0.0836 | 13.02663 | 19.67 |
| 10.8529 | 198.13 | 0.0836 | 8.1522 | 2.29 |
| 12.335 | 5063.34 | 0.1004 | 7.17583 | 58.4 |
| 14.4566 | 8669.85 | 0.0836 | 6.12715 | 100 |
| 16.3983 | 470.36 | 0.0669 | 5.40575 | 5.43 |
| 16.9757 | 538.35 | 0.1004 | 5.22316 | 6.21 |
| 17.416 | 257.63 | 0.0836 | 5.0921 | 2.97 |
| 19.7905 | 2007.61 | 0.0836 | 4.48617 | 23.16 |
| 20.2548 | 1434.71 | 0.1004 | 4.38438 | 16.55 |
| 20.6152 | 1169.49 | 0.0669 | 4.30852 | 13.49 |
| 21.0132 | 3793.73 | 0.1171 | 4.22782 | 43.76 |
| 21.7146 | 6282.16 | 0.1004 | 4.09281 | 72.46 |
| 22.7615 | 3239.73 | 0.1004 | 3.90688 | 37.37 |
| 23.0013 | 484.28 | 0.1004 | 3.86669 | 5.59 |
| 23.3254 | 431.06 | 0.1171 | 3.81369 | 4.97 |
| 24.7187 | 758.12 | 0.0669 | 3.60179 | 8.74 |
| 25.8948 | 817.29 | 0.1506 | 3.44081 | 9.43 |
| 27.0823 | 4235.59 | 0.0836 | 3.29258 | 48.85 |
| 28.6898 | 652.33 | 0.0836 | 3.11165 | 7.52 |
| 29.0316 | 4396.74 | 0.0836 | 3.07579 | 50.71 |
| 30.4594 | 133.22 | 0.0836 | 2.93479 | 1.54 |
| 31.2926 | 291.4 | 0.1004 | 2.85852 | 3.36 |
| 31.6493 | 267.88 | 0.0836 | 2.82711 | 3.09 |
| 32.3162 | 129.32 | 0.1004 | 2.77028 | 1.49 |

TABLE 2-continued

XRPD Peaks for (N,N-Diethylcarbamoyl)methyl methyl (2E)but-2-ene-1,4-dioate: Form 1

| Pos. [°2Th.] | Height [cts] | FWHM [°2Th.] | d-spacing [Å] | Rel. Int. [%] |
|---|---|---|---|---|
| 32.7633 | 277.88 | 0.1171 | 2.73349 | 3.21 |
| 33.5857 | 76.32 | 0.1004 | 2.66841 | 0.88 |
| 34.026 | 399.82 | 0.0502 | 2.63488 | 4.61 |
| 35.3367 | 73.67 | 0.1338 | 2.5401 | 0.85 |
| 35.6451 | 86.4 | 0.1004 | 2.51882 | 1 |
| 37.1955 | 121.88 | 0.0502 | 2.41732 | 1.41 |
| 38.2248 | 40.9 | 0.2007 | 2.35456 | 0.47 |
| 39.0281 | 109.27 | 0.0836 | 2.30793 | 1.26 |

While the entire diffractogram of FIG. 1 can be used to characterize form 1, form 1 can also be accurately characterized with a subset of that data.

In certain embodiments, form 1 of (N,N-Diethylcarbamoyl)methyl methyl (2E)but-2-ene-1,4-dioate exhibits characteristic scattering angles (2θ) at least at 14.5±0.2°, 21.7±0.2°, 12.3±0.2°, 29.0±0.2°, and 27.1±0.2° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.2°, 21.7±0.2°, 12.3±0.2°, 29.0±0.2°, 27.1±0.2°, 21.0±0.2°, 22.8±0.2°, 19.8±0.2°, 6.8±0.2°, and 20.3±0.2° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.2°, 21.7±0.2°, 12.3±0.2°, 29.0±0.2°, 27.1±0.2°, 21.0±0.2°, 22.8±0.2°, 19.8±0.2°, 6.8±0.2°, 20.3±0.2°, 20.6±0.2°, 25.9±0.2°, 24.7±0.2°, 28.7±0.2° and 17.0±0.2° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.1°, 21.7±0.1°, 12.3±0.1°, 29.0±0.1°, and 27.1±0.1° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.1°, 21.7±0.1°, 12.3±0.1°, 29.0±0.1°, 27.1±0.1°, 21.0±0.1°, 22.8±0.1°, 19.8±0.1°, 6.8±0.1° and 20.3±0.1° in an X-ray powder diffraction pattern measured using Cu—K$_\alpha$ radiation.

In certain embodiments, form 1 of (N,N-Diethylcarbamoyl)methyl methyl (2E)but-2-ene-1,4-dioate exhibits characteristic scattering angles (2θ) at least at 14.5±0.1°, 21.7±0.1°, 12.3±0.1°, 29.0±0.1°, 27.1±0.1°, 21.0±0.1°, 22.8±0.1°, 19.8±0.1°, 6.8±0.1°, 20.3±0.1°, 20.6±0.1°, 25.9±0.1°, 24.7±0.1°, 28.7±0.1° and 17.0±0.1° in an X-ray powder diffraction pattern measured using Cu—K$_\alpha$ radiation.

Figure 2:
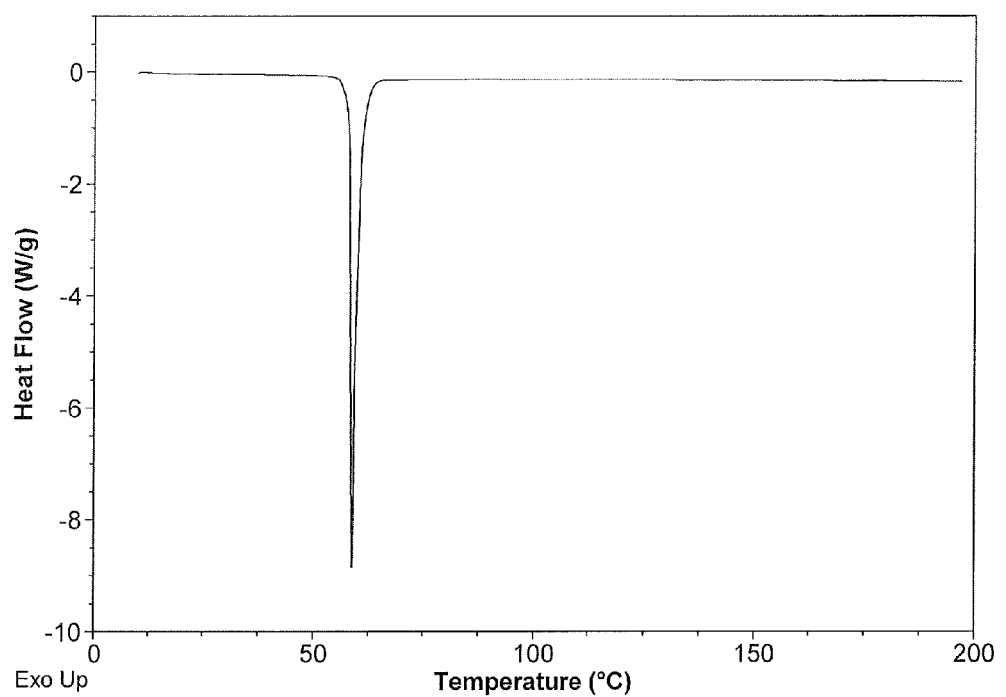
FIG. 2 is a differential scanning calorimetry (DSC) thermogram of a crystalline form 1 of (N,N-Diethylcarbamoyl)methyl methyl (2E)but-2-ene-1,4-dioate.

FIG. 2 is a differential scanning calorimetry (DSC) thermogram of form 1 of the (N,N-Diethylcarbamoyl)methyl methyl (2E)but-2-ene-1,4-dioate. The thermogram shows the form 1 has a melting point of about 58° C.

Figure 3:
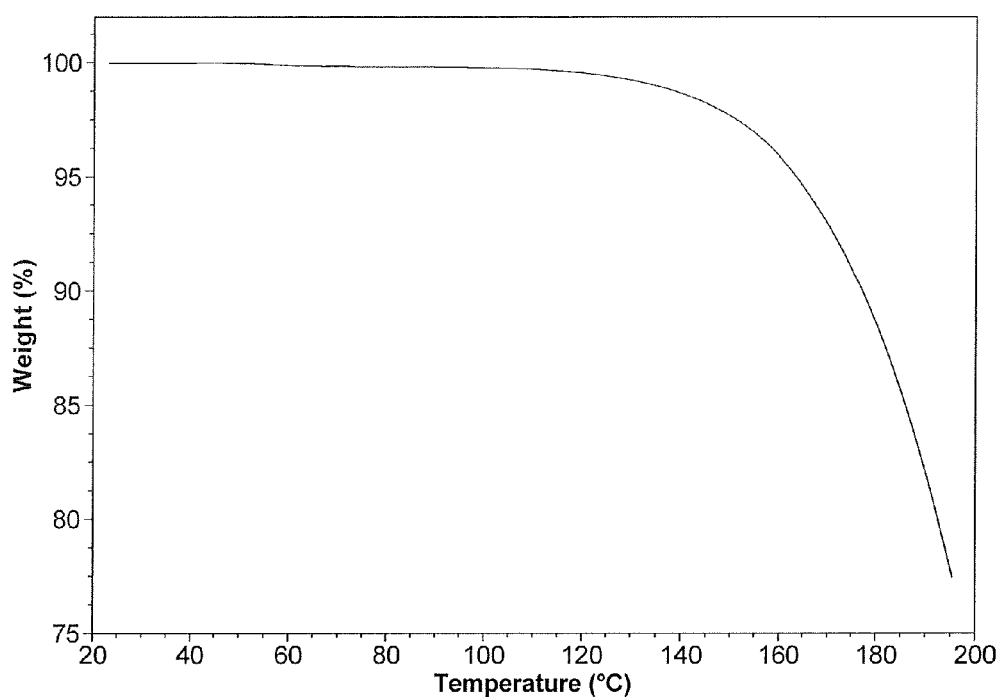
FIG. 3 is thermal gravimetric analysis (TGA) thermogram of a crystalline form 1 of (N,N-Diethylcarbamoyl)methyl methyl (2E)but-2-ene-1,4-dioate.

FIG. 3 is a thermal gravimetric analysis (TGA) thermogram of crystalline form 1 of (N,N-Diethylcarbamoyl)methyl methyl (2E)but-2-ene-1,4-dioate.

(N,N-Diethylcarbamoyl)methyl methyl (2E)but-2-ene-1,4-dioate: Form 2

One crystalline form disclosed herein is form 2 of (N,N-Diethylcarbamoyl)methyl methyl (2E)but-2-ene-1,4-dioate. Differential scanning calorimetry (DSC) analysis of this form 2 shows a melting point between about 48° C. and about 52° C., in certain embodiments between about 49° C. and about 51° C., and in certain embodiments at about 50° C.

The purity of crystalline form 2 of (N,N-Diethylcarbamoyl)methyl methyl (2E)but-2-ene-1,4-dioate is at least 99 wt % as measured by HPLC. In certain embodiments the purity of crystalline form 2 is at least 99.5 wt % as measured by HPLC. In certain embodiments the purity of crystalline form 2 is at least 99.9 wt % as measured by HPLC.

Figure 4:
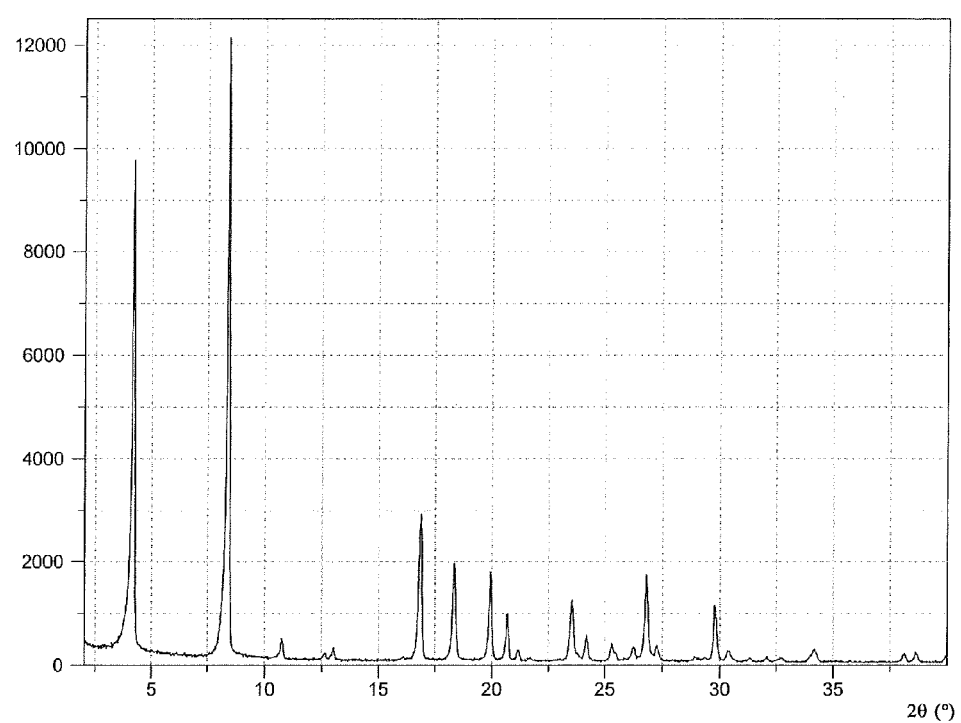
FIG. 4 is an X-ray powder diffractogram (XRPD) of a crystalline form 2 of (N,N-Diethylcarbamoyl)methyl methyl (2E)but-2-ene-1,4-dioate.

FIG. 4 is an X-ray powder diffractogram (XRPD) of form 2 of (N,N-Diethylcarbamoyl)methyl methyl (2E)but-2-ene-1,4-dioate showing the diffraction pattern measured using Cu—K$_\alpha$ radiation. Table 3 lists the approximate numerical values of the XRPD peak positions of the FIG. 4 diffractogram.

TABLE 3

XRPD Peaks for (N,N-Diethylcarbamoyl)methyl methyl (2E)but-2-ene-1,4-dioate: Form 2

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 8.4278 | 11312.51 | 0.1171 | 10.49174 | 100 |
| 4.215 | 9229.54 | 0.1004 | 20.96408 | 81.59 |
| 16.8927 | 2677.65 | 0.184 | 5.24863 | 23.67 |
| 18.3421 | 1829.76 | 0.1338 | 4.83704 | 16.17 |
| 19.94 | 1677.6 | 0.1338 | 4.45287 | 14.83 |
| Peaks (All) | | | | |
| 4.215 | 9229.54 | 0.1004 | 20.96408 | 81.59 |
| 8.4278 | 11312.51 | 0.1171 | 10.49174 | 100 |
| 10.7747 | 375.29 | 0.1004 | 8.2112 | 3.32 |
| 12.6323 | 114.89 | 0.1004 | 7.00762 | 1.02 |
| 13.023 | 215.68 | 0.0669 | 6.79824 | 1.91 |
| 16.8927 | 2677.65 | 0.184 | 5.24863 | 23.67 |
| 18.3421 | 1829.76 | 0.1338 | 4.83704 | 16.17 |
| 19.94 | 1677.6 | 0.1338 | 4.45287 | 14.83 |
| 20.6716 | 906.31 | 0.1004 | 4.29691 | 8.01 |
| 21.1191 | 180.15 | 0.1171 | 4.20685 | 1.59 |
| 23.5364 | 1174.76 | 0.1673 | 3.77998 | 10.38 |
| 24.1612 | 475.39 | 0.0836 | 3.68363 | 4.2 |
| 25.2828 | 322.32 | 0.0836 | 3.5227 | 2.85 |
| 26.2305 | 257.88 | 0.1506 | 3.39754 | 2.28 |
| 26.8051 | 1668.51 | 0.1506 | 3.326 | 14.75 |
| 27.271 | 298.92 | 0.1004 | 3.27023 | 2.64 |
| 28.9259 | 81.8 | 0.1004 | 3.08679 | 0.72 |
| 29.7727 | 1023.91 | 0.102 | 2.99841 | 9.05 |
| 29.849 | 862.49 | 0.0612 | 2.99835 | 7.62 |
| 30.3802 | 197.39 | 0.204 | 2.93982 | 1.74 |
| 31.3336 | 54.91 | 0.1224 | 2.85251 | 0.49 |
| 32.0775 | 76.44 | 0.1224 | 2.78803 | 0.68 |
| 32.7483 | 60.19 | 0.3672 | 2.73244 | 0.53 |
| 34.1585 | 232.57 | 0.1224 | 2.62279 | 2.06 |
| 38.0932 | 161.38 | 0.1224 | 2.36044 | 1.43 |
| 38.6274 | 167.17 | 0.204 | 2.32901 | 1.48 |

While the entire diffractogram of FIG. 4 can be used to characterize form 2, form 2 can also be accurately characterized with a subset of that data.

In certain embodiments, form 2 of (N,N-Diethylcarbamoyl)methyl methyl (2E)but-2-ene-1,4-dioate exhibits characteristic scattering angles (2θ) at least at 8.4±0.2°, 4.2±0.2°, 16.9±0.2°, 18.3±0.2°, and 20.0±0.2° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.2°, 4.2±0.2°, 16.9±0.2°, 18.3±0.2°, 20.0±0.2°, 26.8±0.2°, 23.5±0.2°, 29.8±0.2°, 20.7±0.2°, and 24.2±0.2° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.2°, 4.2±0.2°, 16.9±0.2°, 18.3±0.2°, 20.0±0.2°, 26.8±0.2°, 23.5±0.2°, 29.8±0.2°, 20.7±0.2°, 24.2±0.2°, 10.8±0.2°, 25.3±0.2°, 27.3±0.2°, 26.2±0.2° and 34.2±0.2° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.1°, 4.2±0.1°, 16.9±0.1°, 18.3±0.1°, and 20.0±0.1° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.1°, 4.2±0.1°, 16.9±0.1°, 18.3±0.1°, 20.0±0.1°, 26.8±0.1°, 23.5±0.1°, 29.8±0.1°, 20.7±0.1° and 24.2±0.1° in an X-ray powder diffraction pattern measured using Cu—K$_\alpha$ radiation.

In certain embodiments, form 2 of (N,N-Diethylcarbamoyl)methyl methyl (2E)but-2-ene-1,4-dioate exhibits characteristic scattering angles (2θ) at least at 8.4±0.1°, 4.2±0.1°, 16.9±0.1°, 18.3±0.1°, 20.0±0.1°, 26.8±0.1°, 23.5±0.1°, 29.8±0.1°, 20.7±0.1°, 24.2±0.1°, 10.8±0.1°, 25.3±0.1°, 27.3±0.1°, 26.2±0.1° and 34.2±0.1° in an X-ray powder diffraction pattern measured using Cu—K$_\alpha$ radiation.

Figure 5:
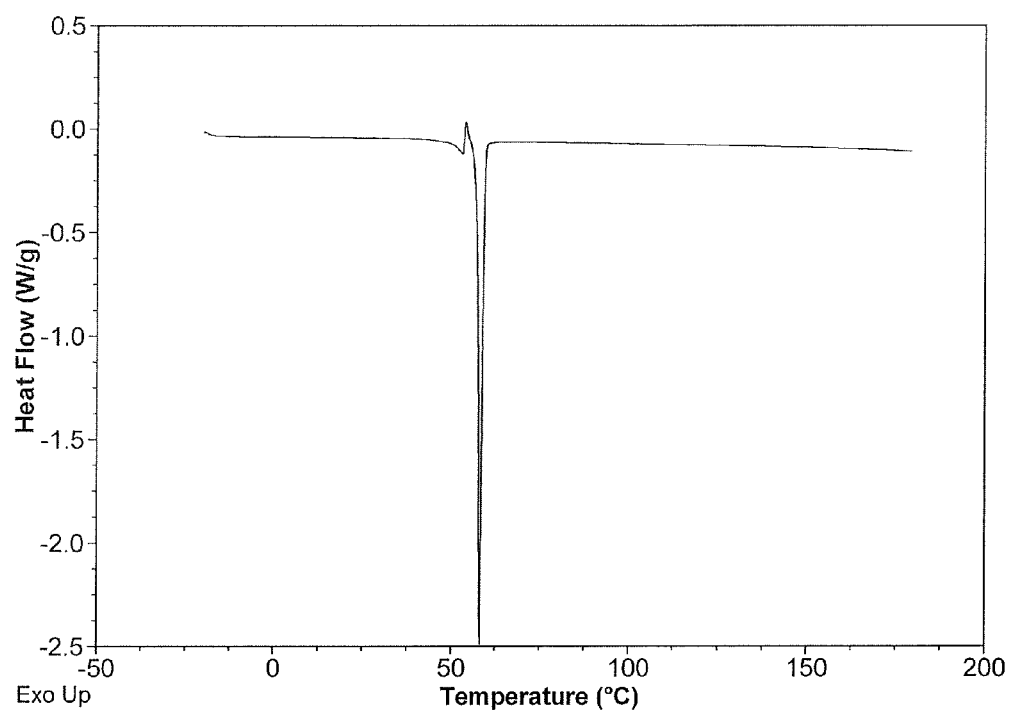
FIG. 5 is a differential scanning calorimetry (DSC) thermogram of a crystalline form 2 of (N,N-Diethylcarbamoyl)methyl methyl (2E)but-2-ene-1,4-dioate.

FIG. 5 is a differential scanning calorimetry (DSC) thermogram of form 2 of the (N,N-Diethylcarbamoyl)methyl methyl (2E)but-2-ene-1,4-dioate. The thermogram shows form 2 has a melting point of about 50° C.

Figure 6:
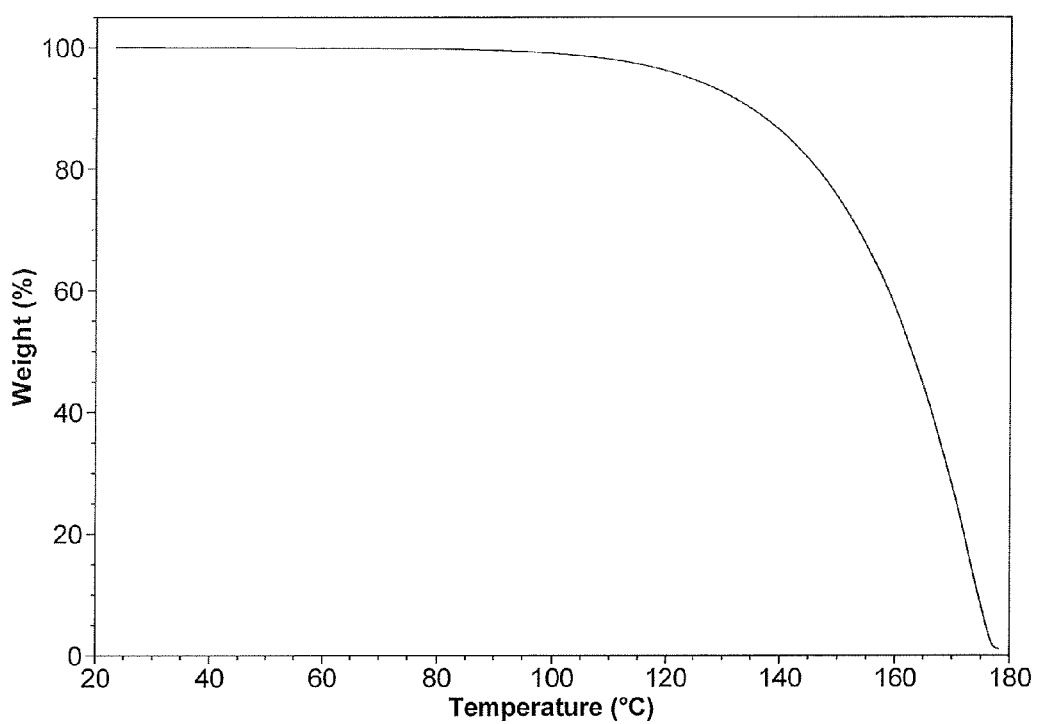
FIG. 6 is thermal gravimetric analysis (TGA) thermogram of a crystalline form 2 of (N,N-Diethylcarbamoyl)methyl methyl (2E)but-2-ene-1,4-dioate.

FIG. 6 is a thermal gravimetric analysis (TGA) thermogram of crystalline form 2 of (N,N-Diethylcarbamoyl)methyl methyl (2E)but-2-ene-1,4-dioate.

(N,N-Diethylcarbamoyl)methyl methyl (2E)but-2-ene-1,4-dioate: Form 3

One crystalline form disclosed herein is form 3 of (N,N-Diethylcarbamoyl)methyl methyl (2E)but-2-ene-1,4-dioate. Differential scanning calorimetry (DSC) analysis of this form 3 shows a melting point between about 45° C. and about 49° C., in certain embodiments between about 46° C. and about 48° C., and in certain embodiments at about 47° C.

The purity of crystalline form 3 of (N,N-Diethylcarbamoyl)methyl methyl (2E)but-2-ene-1,4-dioate is at least 99 wt % as measured by HPLC. In certain embodiments the purity of crystalline form 3 is at least 99.5 wt % as measured by HPLC. In certain embodiments the purity of crystalline form 3 is at least 99.9 wt % as measured by HPLC.

Figure 7:
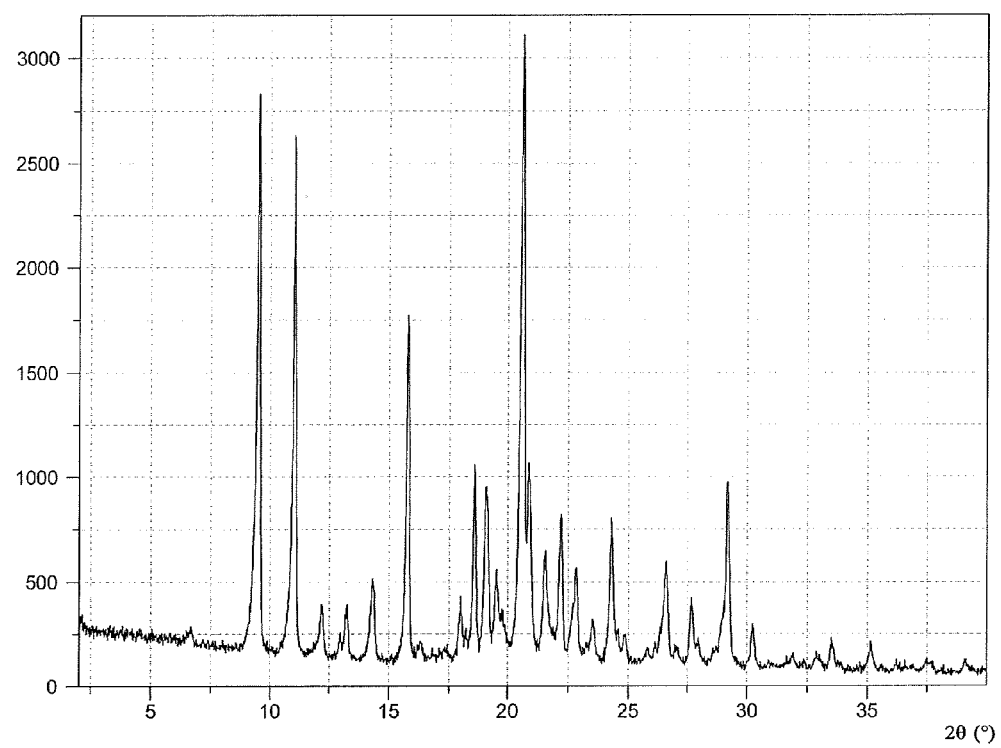
FIG. 7 is an X-ray powder diffractogram (XRPD) of a crystalline form 3 of (N,N-Diethylcarbamoyl)methyl methyl (2E)but-2-ene-1,4-dioate.

FIG. 7 is an X-ray powder diffractogram (XRPD) of form 3 of (N,N-Diethylcarbamoyl)methyl methyl (2E)but-2-ene-1,4-dioate showing the diffraction pattern measured using Cu—K$_\alpha$ radiation. Table 4 lists the approximate numerical values of the XRPD peak positions of the FIG. 7 diffractogram.

TABLE 4

XRPD Peaks for (N,N-Diethylcarbamoyl)methyl methyl (2E)but-2-ene-1,4-dioate: Form 3

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 20.6122 | 2941.88 | 0.1338 | 4.30916 | 100 |
| 9.5381 | 2619.16 | 0.1004 | 9.27285 | 89.03 |
| 11.0718 | 2440.32 | 0.1004 | 7.99154 | 82.95 |
| 15.8074 | 1610.75 | 0.1004 | 5.60648 | 54.75 |
| 18.5914 | 933.36 | 0.1338 | 4.77272 | 31.73 |
| Peaks (All) | | | | |
| 9.5381 | 2619.16 | 0.1004 | 9.27285 | 89.03 |
| 11.0718 | 2440.32 | 0.1004 | 7.99154 | 82.95 |
| 12.2024 | 217.18 | 0.1338 | 7.25351 | 7.38 |
| 13.2605 | 219.31 | 0.1171 | 6.677 | 7.45 |
| 14.3131 | 381.18 | 0.1506 | 6.18824 | 12.96 |
| 15.8074 | 1610.75 | 0.1004 | 5.60648 | 54.75 |
| 16.3081 | 78.28 | 0.2007 | 5.43546 | 2.66 |
| 18.0005 | 290 | 0.1673 | 4.92804 | 9.86 |
| 18.5914 | 933.36 | 0.1338 | 4.77272 | 31.73 |
| 19.059 | 829.03 | 0.0836 | 4.65666 | 28.18 |
| 19.5156 | 398.86 | 0.1171 | 4.54874 | 13.56 |
| 20.6122 | 2941.88 | 0.1338 | 4.30916 | 100 |
| 20.849 | 911.14 | 0.1171 | 4.26073 | 30.97 |
| 21.5204 | 505.59 | 0.1171 | 4.12931 | 17.19 |
| 22.191 | 706.92 | 0.1171 | 4.00602 | 24.03 |
| 22.8235 | 454.03 | 0.1171 | 3.89642 | 15.43 |
| 23.5381 | 206.41 | 0.1506 | 3.77971 | 7.02 |
| 24.3024 | 685.9 | 0.1338 | 3.66254 | 23.31 |
| 24.8546 | 140.84 | 0.1338 | 3.58241 | 4.79 |
| 26.6025 | 506.3 | 0.1506 | 3.35087 | 17.21 |
| 27.6745 | 302.27 | 0.1338 | 3.22345 | 10.27 |
| 29.1631 | 876.91 | 0.1338 | 3.06222 | 29.81 |
| 30.2144 | 205.43 | 0.1171 | 2.95802 | 6.98 |
| 31.8002 | 44.76 | 0.4015 | 2.81404 | 1.52 |
| 32.9135 | 54.11 | 0.2676 | 2.72136 | 1.84 |
| 33.5305 | 133.79 | 0.1338 | 2.67268 | 4.55 |
| 35.1623 | 123.35 | 0.1338 | 2.5523 | 4.19 |
| 37.5326 | 48.52 | 0.3346 | 2.39638 | 1.65 |
| 39.1007 | 49.52 | 0.2007 | 2.30381 | 1.68 |

While the entire diffractogram of FIG. 7 can be used to characterize form 3, form 3 can also be accurately characterized with a subset of that data.

In certain embodiments, form 3 of (N,N-Diethylcarbamoyl)methyl methyl (2E)but-2-ene-1,4-dioate exhibits characteristic scattering angles (2θ) at least at 20.6±0.2°, 9.5±0.2°, 11.1±0.2°, 15.8±0.2°, and 18.6±0.2° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.2°, 9.5±0.2°, 11.1±0.2°, 15.8±0.2°, 18.6±0.2°, 20.8±0.2°, 29.2±0.2°, 19.1±0.2°, 22.2±0.2°, and 24.3±0.2° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.2°, 9.5±0.2°, 11.1±0.2°, 15.8±0.2°, 18.6±0.2°, 20.8±0.2°, 29.2±0.2°, 19.1±0.2°, 22.2±0.2°, 24.3±0.2°, 26.6±0.2°, 21.5±0.2°, 22.8±0.2°, 19.5±0.2° and 14.3±0.2° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.1°, 9.5±0.1°, 11.1±0.1°, 15.8±0.1°, and 18.6±0.1° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.1°, 9.5±0.1°, 11.1±0.1°, 15.8±0.1°, 18.6±0.1°, 20.8±0.1°, 29.2±0.1°, 19.1±0.1°, 22.2±0.1°, and 24.3±0.1° in an X-ray powder diffraction pattern measured using Cu—K$_\alpha$ radiation.

In certain embodiments, form 3 of (N,N-Diethylcarbamoyl)methyl methyl (2E)but-2-ene-1,4-dioate exhibits characteristic scattering angles (2θ) at least at 20.6±0.1°, 9.5±0.1°, 11.1±0.1°, 15.8±0.1°, 18.6±0.1°, 20.8±0.1°, 29.2±0.1°, 19.1±0.1°, 22.2±0.1°, 24.3±0.1°, 26.6±0.1°, 21.5±0.1°, 22.8±0.1°, 19.5±0.1° and 14.3±0.1° in an X-ray powder diffraction pattern measured using Cu—K$_\alpha$ radiation.

Figure 8:
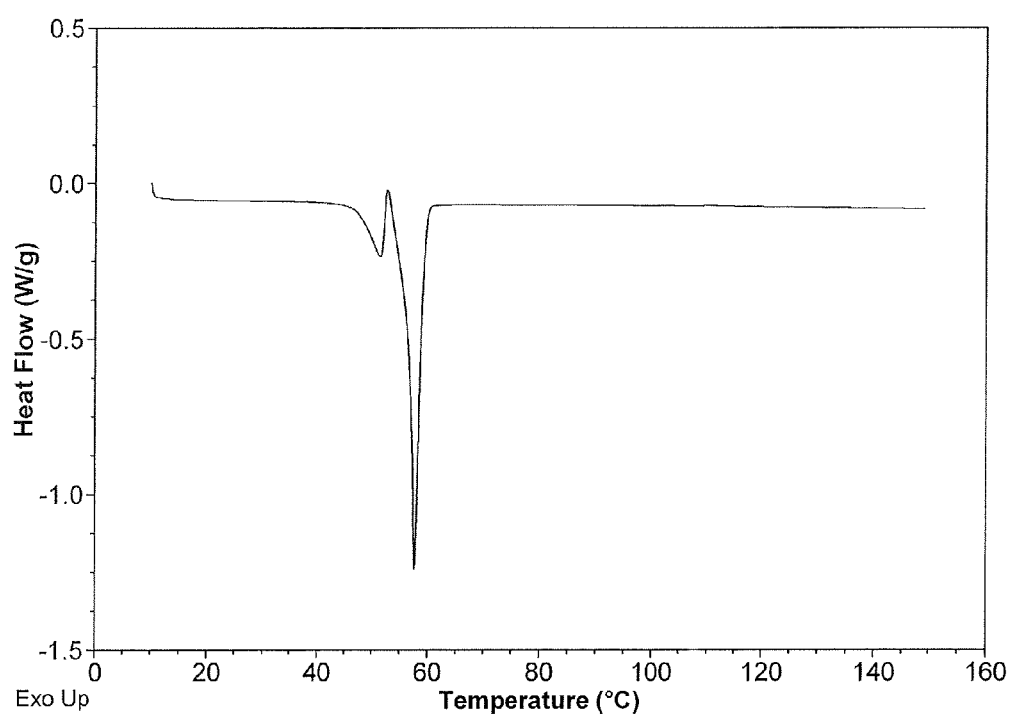
FIG. 8 is a differential scanning calorimetry (DSC) thermogram of a crystalline form 3 of (N,N-Diethylcarbamoyl)methyl methyl (2E)but-2-ene-1,4-dioate.

FIG. 8 is a differential scanning calorimetry (DSC) thermogram of form 3 of the (N,N-Diethylcarbamoyl)methyl methyl (2E)but-2-ene-1,4-dioate. The thermogram shows the form 3 has a melting point of about 47° C.

Figure 9:
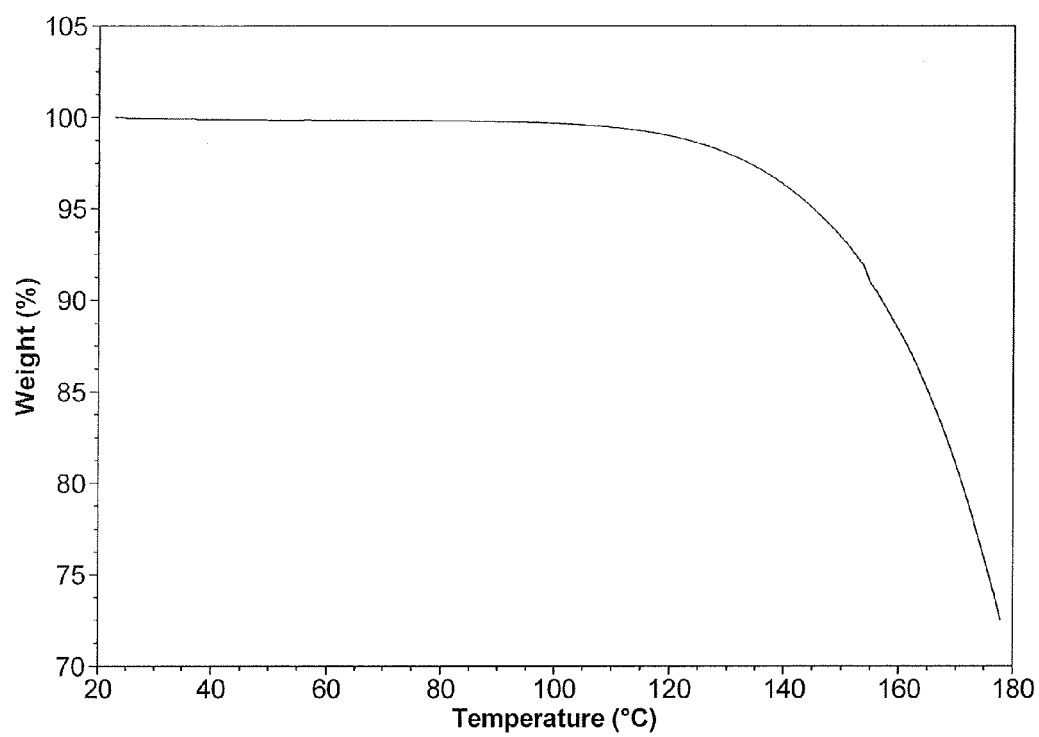
FIG. 9 is thermal gravimetric analysis (TGA) thermogram of a crystalline form 3 of (N,N-Diethylcarbamoyl)methyl methyl (2E)but-2-ene-1,4-dioate.

FIG. 9 is a thermal gravimetric analysis (TGA) thermogram of crystalline form 3 of (N,N-Diethylcarbamoyl)methyl methyl (2E)but-2-ene-1,4-dioate.

(N,N-Diethylcarbamoyl)methyl methyl (2E)but-2-ene-1,4-dioate: Form 4

One crystalline form disclosed herein is form 4 of (N,N-Diethylcarbamoyl)methyl methyl (2E)but-2-ene-1,4-dioate. Differential scanning calorimetry (DSC) analysis of this form 4 shows a polymorphic transformation between about 36° C. and about 40° C., in certain embodiments between about 37° C. and about 39° C., and in certain embodiments at about 38° C.

The purity of crystalline form 4 of (N,N-Diethylcarbamoyl)methyl methyl (2E)but-2-ene-1,4-dioate is at least 99 wt % as measured by HPLC. In certain embodiments the purity of crystalline form 4 is at least 99.5 wt % as measured by HPLC. In certain embodiments the purity of crystalline form 4 is at least 99.9 wt % as measured by HPLC.

Figure 10:
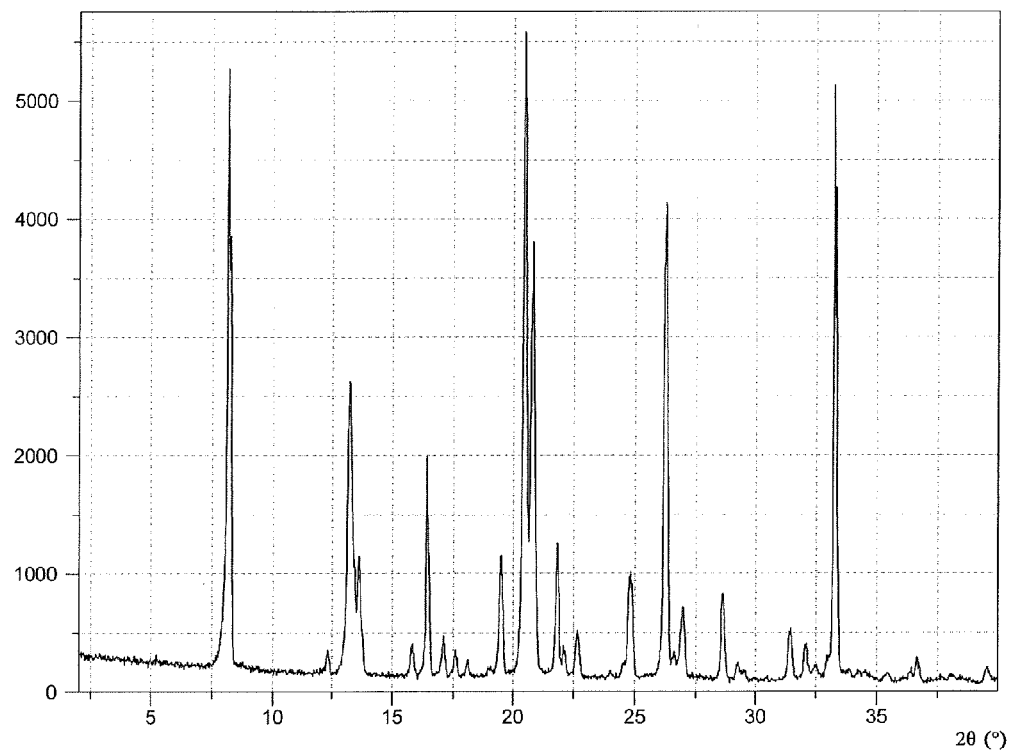
FIG. 10 is an X-ray powder diffractogram (XRPD) of a crystalline form 4 of (N,N-Diethylcarbamoyl)methyl methyl (2E)but-2-ene-1,4-dioate.

FIG. 10 is an X-ray powder diffractogram (XRPD) of form 4 of the (N,N-Diethylcarbamoyl)methyl methyl (2E)but-2-ene-1,4-dioate showing the diffraction pattern measured using Cu—K$_\alpha$ radiation. Table 5 lists the approximate numerical values of the XRPD peak positions of the FIG. 10 diffractogram.

Table 5: XRPD Peaks for (N,N-Diethylcarbamoyl)methyl methyl (2E)but-2-ene-1,4-dioate: Form 4

TABLE 5

XRPD Peaks for (N,N-Diethylcarbamoyl)methyl methyl (2E)but-2-ene-1,4-fioate: Form 4

| Pos. [°2Th.] | Height [cts] | FWHM [°2Th.] | d-spacing [Å] | Rel. Int. [%] |
|---|---|---|---|---|
| Peaks (5 Highest Peaks) | | | | |
| 20.4421 | 5428.16 | 0.1338 | 4.34461 | 100 |
| 8.1616 | 5069.85 | 0.0669 | 10.8333 | 93.4 |
| 33.2225 | 4743.54 | 0.0502 | 2.69675 | 87.39 |
| 26.2929 | 4071.97 | 0.0669 | 3.38962 | 75.02 |
| 20.8019 | 3710.75 | 0.0836 | 4.27029 | 68.36 |
| Peaks (All) | | | | |
| 8.1616 | 5069.85 | 0.0669 | 10.8333 | 93.4 |
| 8.2731 | 3453.55 | 0.0502 | 10.68762 | 63.62 |
| 12.3278 | 178.49 | 0.1338 | 7.17997 | 3.29 |
| 13.1556 | 2023.81 | 0.1673 | 6.73003 | 37.28 |

TABLE 5-continued

XRPD Peaks for (N,N-Diethylcarbamoyl)methyl methyl (2E)but-2-ene-1,4-fioate: Form 4

| Pos. [°2Th.] | Height [cts] | FWHM [°2Th.] | d-spacing [Å] | Rel. Int. [%] |
|---|---|---|---|---|
| 13.6427 | 964.42 | 0.0836 | 6.49081 | 17.77 |
| 15.8255 | 262.36 | 0.1506 | 5.6001 | 4.83 |
| 16.4155 | 1677.54 | 0.0502 | 5.40014 | 30.9 |
| 17.1332 | 312.18 | 0.1673 | 5.17549 | 5.75 |
| 17.6134 | 182.86 | 0.1338 | 5.03547 | 3.37 |
| 18.1058 | 119.69 | 0.1004 | 4.89963 | 2.21 |
| 19.4519 | 904.34 | 0.184 | 4.56349 | 16.66 |
| 20.4421 | 5428.16 | 0.1338 | 4.34461 | 100 |
| 20.8019 | 3710.75 | 0.0836 | 4.27029 | 68.36 |
| 21.8182 | 1151.17 | 0.1338 | 4.07361 | 21.21 |
| 22.1297 | 223.05 | 0.1338 | 4.01696 | 4.11 |
| 22.6845 | 376.22 | 0.1506 | 3.91997 | 6.93 |
| 24.7372 | 700.3 | 0.1004 | 3.59914 | 12.9 |
| 26.2091 | 3212.01 | 0.0816 | 3.39745 | 59.17 |
| 26.2929 | 4071.97 | 0.0669 | 3.38962 | 75.02 |
| 26.9684 | 604.96 | 0.184 | 3.30623 | 11.14 |
| 28.6594 | 687.82 | 0.1506 | 3.11488 | 12.67 |
| 29.2511 | 132.28 | 0.1338 | 3.05321 | 2.44 |
| 31.4215 | 403.53 | 0.2007 | 2.84708 | 7.43 |
| 32.0747 | 298.8 | 0.1673 | 2.79058 | 5.5 |
| 33.2225 | 4743.54 | 0.0502 | 2.69675 | 87.39 |
| 35.4358 | 60.12 | 0.2007 | 2.53322 | 1.11 |
| 36.6746 | 177.18 | 0.1673 | 2.45045 | 3.26 |
| 39.5373 | 106.51 | 0.1673 | 2.27938 | 1.96 |

While the entire diffractogram of FIG. 10 can be used to characterize form 4, form 4 can also be accurately characterized with a subset of that data.

In certain embodiments, form 4 of (N,N-Diethylcarbamoyl)methyl methyl (2E)but-2-ene-1,4-dioate exhibits characteristic scattering angles (2θ) at least at 20.4±0.2°, 8.2±0.2°, 33.2±0.2°, 26.3±0.2°, and 20.8±0.2° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.2°, 8.2±0.2°, 33.2±0.2°, 26.3±0.2°, 20.8±0.2°, 8.3±0.2°, 26.2±0.2°, 13.2±0.2°, 16.4±0.2°, and 21.8±0.2° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.2°, 8.2±0.2°, 33.2±0.2°, 26.3±0.2°, 20.8±0.2°, 8.3±0.2°, 26.2±0.2°, 13.2±0.2°, 16.4±0.2°, 21.8±0.2°, 13.6±0.2°, 19.4±0.2°, 24.7±0.2°, 28.7±0.2°, and 27.0±0.2° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.1°, 8.2±0.1°, 33.2±0.1°, 26.3±0.1°, and 20.8±0.1° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.1°, 8.2±0.1°, 33.2±0.1°, 26.3±0.1°, 20.8±0.1°, 8.3±0.1°, 26.2±0.1°, 13.2±0.1°, 16.4±0.1°, and 21.8±0.1° in an X-ray powder diffraction pattern measured using Cu—K$_\alpha$ radiation.

In certain embodiments, form 4 of (N,N-Diethylcarbamoyl)methyl methyl (2E)but-2-ene-1,4-dioate exhibits characteristic scattering angles (2θ) at least at 20.4±0.1°, 8.2±0.1°, 33.2±0.1°, 26.3±0.1°, 20.8±0.1°, 8.3±0.1°, 26.2±0.1°, 13.2±0.1°, 16.4±0.1°, 21.8±0.1°, 13.6±0.1°, 19.4±0.1°, 24.7±0.1°, 28.7±0.1°, and 27.0±0.1° in an X-ray powder diffraction pattern measured using Cu—K$_\alpha$ radiation.

Figure 11:
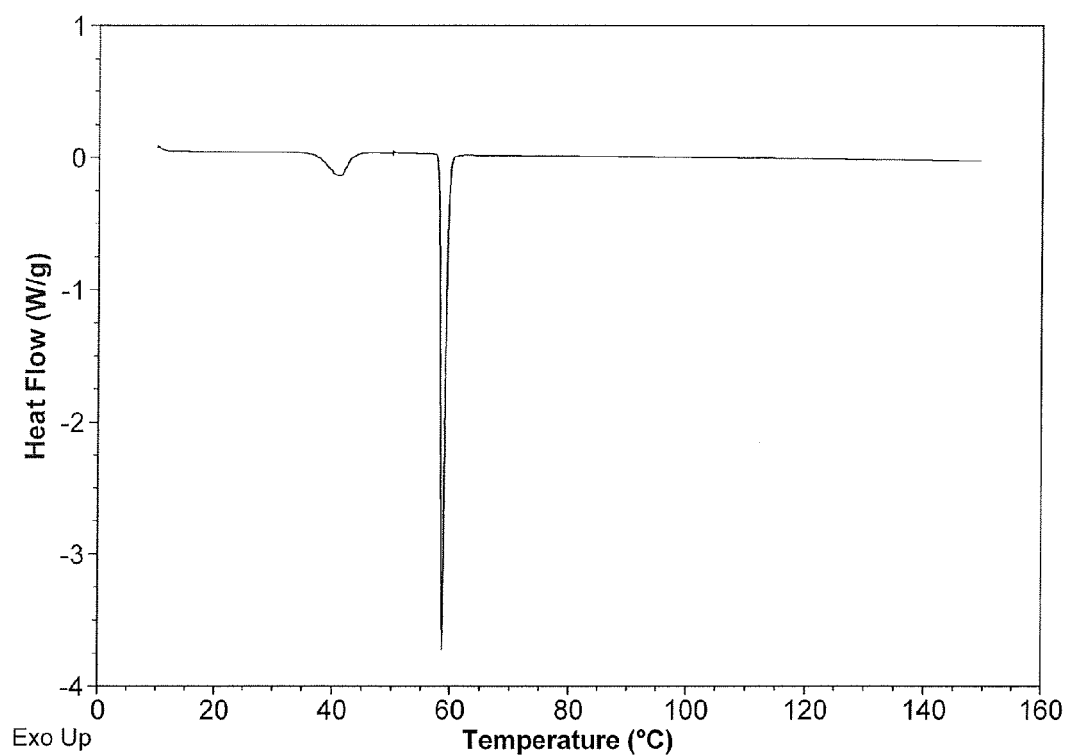
FIG. 11 is a differential scanning calorimetry (DSC) thermogram of a crystalline form 4 of (N,N-Diethylcarbamoyl)methyl methyl (2E)but-2-ene-1,4-dioate.

FIG. 11 is a differential scanning calorimetry (DSC) thermogram of form 4 of the (N,N-Diethylcarbamoyl)methyl methyl (2E)but-2-ene-1,4-dioate. The thermogram shows the form 4 has a melting point of about 38° C.

Figure 12:
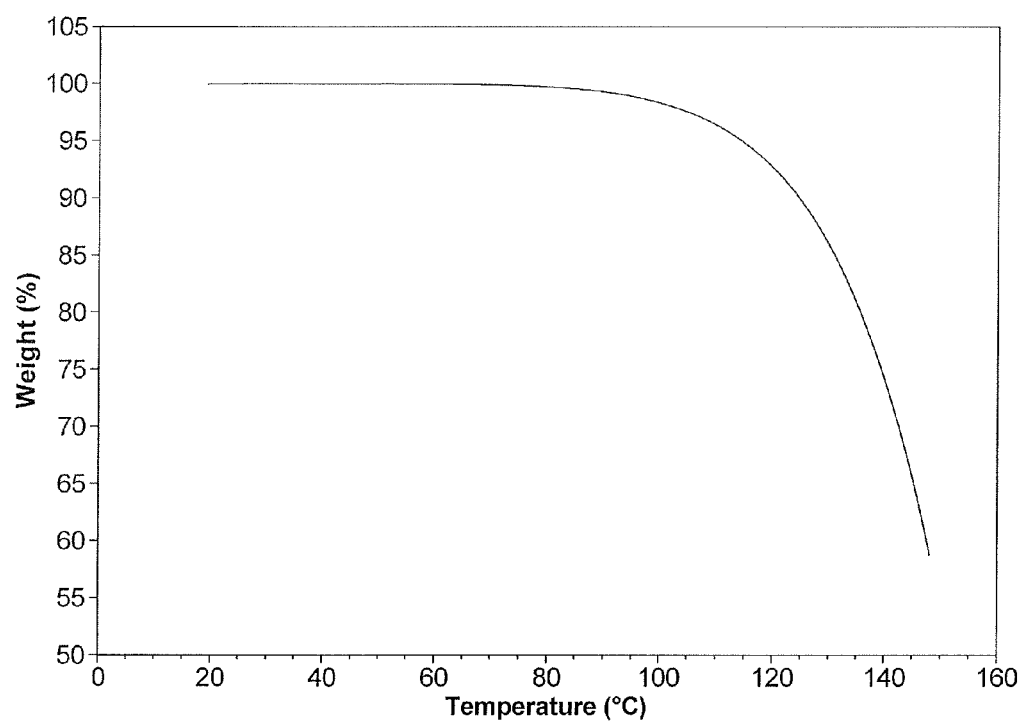
FIG. 12 is thermal gravimetric analysis (TGA) thermogram of a crystalline form 4 of (N,N-Diethylcarbamoyl)methyl methyl (2E)but-2-ene-1,4-dioate.

FIG. 12 is a thermal gravimetric analysis (TGA) thermogram of crystalline form 4 of (N,N-Diethylcarbamoyl)methyl methyl (2E)but-2-ene-1,4-dioate.

Pharmaceutical Compositions

The present disclosure relates to pharmaceutical compositions comprising a therapeutically effective amount of a crystalline form of (N,N-Diethylcarbamoyl)methyl methyl (2E)but-2-ene-1,4-dioate together with a suitable amount of one or more pharmaceutically acceptable vehicle so as to provide a composition for proper administration to a patient. The crystalline form 1, form 2, form 3, and form 4 of (N,N-Diethylcarbamoyl)methyl methyl (2E)but-2-ene-1,4-dioate disclosed herein have the same pharmaceutical activity as the respective active pharmaceutical ingredient (API). Suitable pharmaceutical vehicles are described in the art.

Pharmaceutical compositions for the treatment of any one or more diseases and disorders comprise a therapeutically effective amount of a crystalline form disclosed herein as appropriate for treatment of a patient with the particular disease(s) or disorder(s).

A pharmaceutical composition may be any pharmaceutical form which maintains the crystalline form of a disclosed crystalline form. In certain embodiments, the pharmaceutical composition may be selected from a solid form, a liquid suspension, an injectable composition, a topical form, and a transdermal form.

Depending on the type of pharmaceutical composition, the pharmaceutically acceptable vehicle may be chosen from any one or a combination of vehicles known in the art. The choice of the pharmaceutically acceptable vehicle depends upon the pharmaceutical form and the desired method of administration to be used. For a pharmaceutical composition comprising a crystalline form disclosed herein, a vehicle should be chosen that maintains the crystalline form. In other words, the vehicle should not substantially alter the crystalline form of the crystalline form. For example, a liquid vehicle which would dissolve the crystalline form should not be used. Nor should the vehicle be otherwise incompatible with a crystalline form, such as by producing any undesirable biological effect or otherwise interacting in a deleterious manner with any other component(s) of the pharmaceutical composition.

In some embodiments, the pharmaceutical compositions are formulated in unit dosage forms for ease of administration and uniformity of dosage. A "unit dosage form" refers to a physically discrete unit of therapeutic agent appropriate for the patient to be treated. It will be understood, however, that the total daily dosage of a crystalline form and its pharmaceutical compositions will typically be decided by the attending physician within the scope of sound medical judgment.

Because the crystalline forms disclosed herein are more easily maintained during their preparation, solid dosage forms may be employed in numerous embodiments for the pharmaceutical compositions. In some embodiments, solid dosage forms for oral administration include capsules, tablets, pills, powders, and granules. In such solid dosage forms, the active compound is mixed with at least one inert, pharmaceutically acceptable vehicle such as sodium citrate or dicalcium phosphate. The solid dosage form may also include one or more of: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate. The solid dosage forms may also comprise buffering agents. They may optionally comprise opacifying agents and can also be of a composition such that they release the active ingredient(s) only in a certain part of the intestinal tract, optionally, in a delayed manner. Remington's Pharmaceutical Sciences, Sixteenth Edition, E. W. Martin (Mack Publishing Co., Easton, Pa., 1980) discloses various vehicles used in formulating pharmaceutical compositions and known techniques for the preparation thereof. Solid dosage forms of pharmaceutical compositions can also be prepared with coatings and shells such as enteric coatings and other coatings well known in the pharmaceutical formulating art.

A crystalline form disclosed herein can be in a solid micro-encapsulated form with one or more vehicles as discussed above. Microencapsulated forms of a crystalline form may also be used in soft and hard-filled gelatin capsules with vehicles such as lactose or milk sugar as well as high molecular weight polyethylene glycols and the like.

Also disclosed herein are methods for the treatment of the disorders disclosed herein. The crystalline forms, and pharmaceutical compositions comprising them, may be administered using any amount, any form of pharmaceutical composition and any route of administration effective for the treatment. After formulation with an appropriate pharmaceutically acceptable vehicle in a desired dosage, as known by those of skill in the art, the pharmaceutical compositions can be administered to humans and other animals orally, rectally, parenterally, intravenously, intracisternally, intravaginally, intraperitoneally, topically (as by powders, ointments, or drops), bucally, as an oral or nasal spray, or the like, depending on the location and severity of the condition being treated. In certain embodiments, the crystalline forms may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject.

Therapeutic Uses

The crystalline forms 1, 2, 3, and 4 of (N,N-Diethylcarbamoyl)methyl methyl (2E)but-2-ene-1,4-dioate disclosed herein may be used to treat diseases, disorders, conditions, and/or symptoms of any disease or disorder for which MHF is known to provide, or is later found to provide, therapeutic benefit. MHF is known to be effective in treating psoriasis, multiple sclerosis, an inflammatory bowel disease, asthma, chronic obstructive pulmonary disease, and arthritis, among others. Hence, the crystalline forms 1, 2, 3, and 4 disclosed herein may be used to treat any one or more of the foregoing diseases and disorders. The underlying etiology of any of the foregoing diseases being treated may have a multiplicity of origins. Further, in certain embodiments, a therapeutically effective amount of one or more of the crystalline forms of (N,N-Diethylcarbamoyl)methyl methyl (2E)but-2-ene-1,4-dioate may be administered to a patient, such as a human, as a preventative measure against various diseases or disorders.

The crystalline forms 1, 2, 3, and 4 of (N,N-Diethylcarbamoyl)methyl methyl (2E)but-2-ene-1,4-dioate disclosed herein can be administered to a patient to treat or prevent any one or more of the diseases and conditions selected from: acute dermatitis, acute disseminated encephalomyelitis, Addison's disease, adrenal leukodystrophy, AGE-induced genome damage, Alexanders Disease, alopecia areata (totalis and universalis), Alper's Disease, Alzheimer's disease, amyotrophic lateral sclerosis, angina pectoris, ankylosing spondylitis, antiphospholipid antibody syndrome, arthritis, asthma, autoimmune carditis, autoimmune hemolytic anemia, autoimmune hepatitis, autoimmune inner ear disease, balo concentric sclerosis, Behcet's disease, bullous pemphigoid, Canavan disease, cardiac insufficiency including left ventricular insufficiency, celiac disease, central nervous system vasculitis, Chagas disease, Charcott-Marie-Tooth Disease, childhood ataxia with central nervous system hypomyelination, chronic dermatitis, chronic idiopathic peripheral neuropathy, chronic obstructive pulmonary disease, contact dermatitis, Crohn's disease, cutaneous Crohn's disease, cutaneous lupus, cutaneous sarcoidosis, dermatomyositis, diabetes mellitus type I, diabetic retinopathy, eczema, endometriosis, globoid cell leukodystrophy (Krabbe Disease), Goodpasture's syndrome, graft versus host disease, granulomas including annulaire, Graves' disease, Guillain-Barre syndrome, Hashimoto's disease, hepatitis C viral infection, herpes simplex viral infection, hidradenitis suppurativea, human immunodeficiency viral infection, Huntington's disease, idiopathic thrombocytopenic purpura, IgA neuropathy, inflammatory bowel disease, interstitial cystitis, irritable bowel disorder, ischemia, Kawasaki disease, lichen planus, lupus, lupus erythematosus, macular degeneration, mitochondrial encephalomyopathy, mixed connective tissue disease, monomelic amyotrophy, morphea, multiple sclerosis, myasthenia gravis, myocardial infarction, narcolepsy, neurodegeneration with brain iron accumulation, neuromyelitis optica, neuromyotonia, neurosarcoidosis, NF-κB mediated diseases, optic neuritis, pareneoplastic syndromes, Parkinson's disease, Pelizaeus-Merzbacher disease, pemphigus, pernicious anaemia, polymyositis, primary biliary cirrhosis, primary lateral sclerosis, progressive supranuclear palsy, psoriasis, psoriatic arthritis, pyoderma gangrenosum, reperfusion injury, retinopathia pigmentosa, rheumatica, sarcoidosis, Schilders Disease, schizophrena, scleroderma, Sjogren's syndrome, stiff person syndrome, subacute necrotizing myelopathy, susac syndrome, temporal arteritis, transplantation rejection, transverse myelitis, a tumor, ulcerative colitis, vasculitis, vitiligo, Wegener's granulomatosis and Zellweger's syndrome.

Efficacy of the crystalline forms 1, 2, 3 and 4 of (N,N-Diethylcarbamoyl)methyl methyl (2E)but-2-ene-1,4-dioate for treating any of the diseases and conditions listed can be determined using animal models and in clinical trials.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions.

Fumaric acid esters are recognized for the treatment of psoriasis and dimethyl fumarate is approved for the systemic treatment of psoriasis in Germany (Mrowietz and Asadullah, *Trends Mol Med* (2005), 11(1): 43-48; and Mrowietz et al., *Br J Dermatology* (1999), 141: 424-429).

Efficacy of the crystalline forms 1, 2, 3 and 4 of (N,N-Diethylcarbamoyl)methyl methyl (2E)but-2-ene-1,4-dioate for treating psoriasis can be determined using animal models and in clinical trials.

Multiple Sclerosis

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied, with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, *Lab Invest* (2001), 81: 263-281; and Virley, *NeuroRx* (2005), 2(4): 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances, spasticity, tremor, a lack of coordination, and visual impairment, any one of which negatively impacts the quality of life of the individual. The clinical course of MS can vary from individual to individual, but invariably the disease can be categorized in three forms: relapsing-remitting, secondary progressive, and primary progressive.

Studies support the efficacy of fumaric acid esters for treating MS and fumaric acid esters are presently undergoing phase II clinical testing for such treatment (Schimrigk et al., *Eur J Neurology* (2006), 13: 604-610; and Wakkee and Thio, *Current Opinion Investigational Drugs* (2007), 8(11): 955-962).

Assessment of MS treatment efficacy in clinical trials can be accomplished using tools such as the Expanded Disability Status Scale and the MS Functional, as well as magnetic resonance imaging, lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

The efficacy of the crystalline forms 1, 2, 3, and 4 of (N,N-Diethylcarbamoyl)methyl methyl (2E)but-2-ene-1,4-dioate for treating MS can be determined using animal models and in clinical trials.

EXAMPLES

Example 1: Synthesis, Purification and Analysis of Crystalline Form 1 of (N,N-Diethylcarbamoyl)methyl methyl (2E)but-2-ene-1,4-dioate Crystalline form 1 is the thermodynamically stable form at ambient temperature. Because of that, it can be produced by suspending an excess amount of (N,N-Diethylcarbamoyl)methyl methyl (2E)but-2-ene-1,4-dioate solid in an organic solvent for an extended period of time. For example, the pure form 1 of (N,N-Diethylcarbamoyl)methyl methyl (2E)but-2-ene-1,4-dioate can be produced by suspending 300 mg (N,N-Diethylcarbamoyl)methyl methyl (2E)but-2-ene-1,4-dioate solid in 1 mL tert-butyl ether (MTBE) at room temperature for 24 hours, followed by vacuum filtration and drying.

Differential Scanning Calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimpled lids. A pinhole was made at the center of the lid to avoid any pressure buildup during heating. Samples were equilibrated at 10° C. and ramped at a heating rate of 10° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 2) shows that form 1 of (N,N-Diethylcarbamoyl)methyl methyl (2E)but-2-ene-1,4-dioate first melts at about 58° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 10° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 3) shows that form 1 of N,N-Diethylcarbamoyl)methyl methyl (2E)but-2-ene-1,4-dioate does not undergo any weight loss prior to melting, which indicates that the form 1 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation ($\lambda$=1.54051 Å) with output voltage of 45 kV and current of 40 mA. The instrument adopts a para-focusing Bragg-Brentano geometry with incident divergence and scattering slits set at $\frac{1}{16}°$ and $\frac{1}{8}°$ respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 1 of the (N,N-Diethylcarbamoyl)methyl methyl (2E)but-2-ene-1,4-dioate is shown in FIG. 1. Unless otherwise specified, the experimental data for X-ray powder diffraction were collected at room temperature.

HPLC Analysis

HPLC analysis is performed using an Agilent HPLC, UV detector monitoring at 210 nm wavelength, and an Inertsil ODS-4 C-18 chromatography column (4.6×150 mm, 3 μm particle size) at 35° C., using an injection volume of a 10 μL sample with an approximate concentration of 0.1 mg/mL. The eluent consists of a 30 minute gradient between two separate mobile phases; mobile phase A consisting of water with 0.05% phosphoric acid and mobile phase B consisting of 90% acetonitrile/10% water/0.05% phosphoric acid at a flow rate of 1 ml/min.

| | Gradient | |
| --- | --- | --- |
| Time (min) | % Mobile Phase A | % Mobile Phase B |
| 0 | 98 | 2 |
| 6 | 65 | 35 |
| 15 | 55 | 45 |
| 25 | 10 | 90 |
| 25.1 | 98 | 2 |
| 30 | 98 | 2 |

Example 2: Synthesis, Purification and Analysis of Crystalline Form 2 of (N,N-Diethylcarbamoyl)methyl methyl (2E)but-2-ene-1,4-dioate Approximately 50 mg of N,N-Diethylcarbamoyl)methyl methyl (2E)but-2-ene-1,4-dioate was dissolved completely in 1 mL isopropanol/water (1/1 v/v), followed by evaporation of solvent in a fume hood. The obtained crystals after solvent evaporation were shown to be pure form 2.

Differential Scanning Calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimpled lids. A pinhole was made at the center of the lid to avoid any pressure buildup during heating. Samples were equilibrated at 10° C. and ramped to at a heating rate of 2° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 5) shows that form 2 of (N,N-Diethylcarbamoyl)methyl methyl (2E)but-2-ene-1,4-dioate first melts at about 50° C., followed by recrystallization and melting. The second melting completes at approximately 60° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 2° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 6) shows that form 2 of (N,N-Diethylcarbamoyl)methyl methyl (2E)but-2-ene-1,4-dioate does not undergo any weight loss prior to melting, which indicates that the form 2 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation (2=1.54051 Å) with output voltage of 45 kV and current of 40 mA. The instrument adopts a para-focusing Bragg-Brentano geometry with incident divergence and scattering slits set at $\frac{1}{16}°$ and $\frac{1}{8}°$ respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 2 of the (N,N-Diethylcarbamoyl)methyl methyl (2E)but-2-ene-1,4-dioate is shown in FIG. 4. Unless otherwise specified, the experimental data for X-ray powder diffraction were collected at room temperature.

HPLC Analysis

HPLC analysis is performed as described in Example 1.

Example 3: Synthesis, Purification and Analysis of Crystalline Form 3 of (N,N-Diethylcarbamoyl)methyl methyl (2E)but-2-ene-1,4-dioate Approximately 420 mg of (N,N-Diethylcarbamoyl)methyl methyl (2E)but-2-ene-1,4-dioate was heated in a scintillation vial to 70° C., at which temperature solid (N,N-Diethylcarbamoyl)methyl methyl (2E)but-2-ene-1,4-dioate completely melted. The molten compound was immediately immersed into liquid nitrogen. The resulting solid was shown to be pure form 3.

Differential Scanning Calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimped lids. A pinhole was made at the center of the lid to avoid any pressure buildup during heating. Samples were equilibrated at 10° C. and ramped at a heating rate of 2° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 8) shows that form 3 of (N,N-Diethylcarbamoyl)methyl methyl (2E)but-2-ene-1,4-dioate first melts at about 47° C. The melting is immediately followed by recrystallization and melting. The second melting completes at approximately 60° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 2° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 9) shows that form 3 of (N,N-Diethylcarbamoyl)methyl methyl (2E)but-2-ene-1,4-dioate does not undergo any weight loss prior to melting, which indicates that the Form 3 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation (λ=1.54051 Å) with output voltage of 45 kV and current of 40 mA. The instrument adopts a para-focusing Bragg-Brentano geometry with incident divergence and scattering slits set at 1/16° and 1/8° respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 3 of the (N,N-Diethylcarbamoyl)methyl methyl (2E)but-2-ene-1,4-dioate is shown in FIG. 7. Unless otherwise specified, the experimental data for X-ray powder diffraction were collected at room temperature.

HPLC Analysis

HPLC analysis is performed as described in Example 1.

Example 4: Synthesis, Purification and Analysis of Crystalline Form 4 of (N,N-Diethylcarbamoyl)methyl methyl (2E)but-2-ene-1,4-dioate At a temperature of about 50-70° C., under a nitrogen atmosphere, a slurry of mono-methyl fumarate (130 g), toluene (800 mL) and N,N-diethylchloroacetamide (157 g) is added to triethylamine (1.07 g). The temperature is adjusted to 85-95° C. and maintained there for 4 hours. Then the temperature is then adjusted to 15-25° C. and the mixture is subjected to vigorous agitation. After 30 minutes of vigorous agitation in 200 mL of water, the agitation is stopped and the phases are allowed to separate for 30 minutes. The upper organic phase is washed with additional deionized water (75 mL) with vigorous agitation for 30 minutes. The agitation is then stopped and the phases are allowed to separate for 30 minutes. The organic layer is dried over anhydrous sodium sulfate (25 g) for 2 hours. The reaction is filtered and the solution is cooled to 10-20° C. Heptane (1600 mL), at −5 to −20° C. is added over 5 minutes. The reaction is cooled to −5° C. to −10° C. for 24 to 48 hours. The resulting product is air dried for 12 hours. XRPD analysis confirms product is form 4.

Differential Scanning Calorimetry (DSC) Analysis

DSC analysis was conducted using a TA Instruments Q2000 DSC equipped with a refrigerated cooling system. For all DSC analyses, 2-5 mg of sample was loaded into $T_{zero}$ aluminum pans with crimped lids. A pinhole was made at the center of the lid to avoid any pressure buildup during heating. Samples were equilibrated at 10° C. and ramped to a rate of 2° C. per minute under a purge of dry nitrogen gas. The data acquisition was controlled by Thermal Advantage software Release 4.9.1. The data were analyzed with Universal Analysis 2000 software (version 4.5A).

The DSC thermogram (FIG. 11) shows that form 4 of (N,N-Diethylcarbamoyl)methyl methyl (2E)but-2-ene-1,4-dioate undergoes a solid-solid phase transformation at approximately 38° C. The resulting solid melts at approximately 58° C.

Thermogravimetric Analysis (TGA)

Thermal gravimetric analysis was conducted using a TA Instruments Q5000 thermogravimetric analyzer. For all TGA analyses, 5-10 mg of sample was loaded onto a platinum pan and heated at a rate of 2° C. per minute under a purge of dry nitrogen gas. The data acquisition was controlled by Thermal Advantage software Release 4.9.1. The data was analyzed with Universal Analysis 2000 software (version 4.5A).

The TGA thermogram (FIG. 12) shows that form 4 of (N,N-Diethylcarbamoyl)methyl methyl (2E)but-2-ene-1,4-dioate does not undergo any weight loss prior to melting, which indicates that the form 4 is an anhydrous crystalline solid.

X-Ray Powder Diffraction (XRPD) Analysis

Powder X-ray diffraction analysis was performed using a PANalytical X'Pert Pro X-ray diffractometer. The X-ray source was Cu $K_\alpha$ radiation ($\lambda$=1.54051 Å) with output voltage of 45 kV and current of 40 mA. The instrument adopts a para-focusing Bragg-Brentano geometry with incident divergence and scattering slits set at $\frac{1}{16}°$ and $\frac{1}{8}°$ respectively. Large Soller slits (0.04 rad) were used for both incident and diffracted beam to remove axial divergence. A small amount of powder (9-12 mg) was gently pressed onto the single crystal silicon sample holder to form a smooth surface, and samples were subjected to spinning at a rate of two revolutions per second, throughout the acquisition process. The samples were scanned from 2° to 40° in 2θ with a step size of 0.017° and a scan speed of 0.067°/sec. The data acquisition was controlled and analyzed by X'Pert Data Collector (version 2.2d) and X'Pert Data Viewer (version 1.2c), respectively.

The X-ray diffraction pattern for form 4 of the (N,N-Diethylcarbamoyl)methyl methyl (2E)but-2-ene-1,4-dioate is shown in FIG. 10. Unless otherwise specified, the experimental data for X-ray powder diffraction were collected at room temperature.

HPLC Analysis

HPLC analysis is performed as described in Example 1.

What is claimed is:

1. A method of making a pharmaceutical composition comprising combining crystalline (N,N-Diethylcarbamoyl)methyl methyl (2E)but-2-ene-1,4-dioate having a purity of at least 99% by weight as measured by HPLC and a pharmaceutically acceptable vehicle;
   wherein the crystalline (N,N-Diethylcarbamoyl)methyl methyl (2E)but-2-ene-1,4-dioate is selected from crystalline form 2, crystalline form 3 and crystalline form 4;
   crystalline form 2 exhibits characteristic scattering angles (2θ) at least at 8.4±0.2°, 4.2±0.2°, 16.9±0.2°, 18.3±0.2°, and 20.0±0.2° in an X-ray powder diffraction pattern measured using Cu-Kα radiation;
   crystalline form 3 exhibits characteristic scattering angle (2θ) at least at 20.6±0.2°, 9.5±0.2°, 11.1±0.2°, 15.8±0.2° and 18.6±0.2° in an X-ray powder diffraction pattern measured using Cu—Kα radiation; and
   crystalline form 4 exhibits characteristic scattering angle (2θ) at least at 20.4±0.2°, 8.2±0.2°, 33.2±0.2°, 26.3±0.2°, and 20.8±0.2° in an X-ray powder diffraction pattern measured using Cu—Kα radiation.

2. The method of claim 1, wherein the crystalline form is form 2 having a DSC thermogram peak of between about 49° C. and about 51° C.

3. The method of claim 1, wherein the crystalline form 2 further comprises characteristic scattering angles (2θ) at 26.8±0.2°, 23.5±0.2°, 29.8±0.2°, 20.7±0.2° and 24.2±0.2° in an X-ray powder diffraction pattern measured using Cu—Kα radiation.

4. The method of claim 1, wherein the crystalline form is form 3 having a DSC thermogram peak of between about 46° C. and about 48° C.

5. The method of claim 1, wherein the crystalline form 3 further comprises characteristic scattering angles (2θ) at 20.8±0.1°, 29.2±0.1°, 19.1±0.1°, 22.2±0.1° and 24.3±0.1° in an X-ray powder diffraction pattern measured using Cu—Kα radiation.

6. The method of claim 1, wherein the crystalline form is form 4 having a DSC thermogram peak of between about 37° C. and about 39° C.

7. The method of claim 1, wherein the crystalline form 4 further comprises characteristic scattering angles (2θ) at 8.3±0.2°, 26.2±0.2°, 13.2±0.2°, 16.4±0.2° and 21.8±0.2° in an X-ray powder diffraction pattern measured using Cu—Kα radiation.

8. The method of claim 1, wherein the crystalline (N,N-Diethylcarbamoyl)methyl methyl (2E)but-2-ene-1,4-dioate has a purity of at least 99.5% by weight as measured by HPLC.

9. The method of claim 1, wherein the crystalline (N,N-Diethylcarbamoyl)methyl methyl (2E)but-2-ene-1,4-dioate has a purity of at least 99.9% by weight as measured by HPLC.

10. The method of claim 1, wherein the pharmaceutically acceptable vehicle is selected from the group consisting of a diluent, a pharmaceutically acceptable adjuvant, a pharmaceutically acceptable excipient, a pharmaceutically acceptable carrier and a combination thereof.

11. The method of claim 10, wherein the pharmaceutically acceptable vehicle is selected from the group consisting of sodium citrate, dicalcium phosphate and a combination thereof.

12. The method of claim 1, wherein the pharmaceutically acceptable vehicle is selected from the group consisting of starches, lactose, sucrose, glucose, mannitol, silicic acid, carboxymethylcellulose, alginates, gelatin, polyvinylpyrrolidinone, acacia, glycerol, agar-agar, calcium carbonate, potato starch, tapioca starch, alginic acid, certain silicates, sodium carbonate, paraffin, quaternary ammonium compounds, cetyl alcohol, glycerol monostearate, kaolin, bentonite clay, talc, calcium stearate, magnesium stearate, solid polyethylene glycols, sodium lauryl sulfate and a combination thereof.

13. The method of claim 1, wherein the pharmaceutical formulation is an oral dosage form.

14. A method of treating a disease in a patient in need thereof, comprising administering to the patient a therapeutically effective amount of a pharmaceutical composition comprising crystalline (N,N-Diethylcarbamoyl)methyl methyl (2E)but-2-ene-1,4-dioate having a purity of at least 99% by weight as measured by HPLC and a pharmaceutically acceptable vehicle; wherein the disease is selected form the group consisting of multiple sclerosis and psoriasis;
   crystalline (N,N-Diethylcarbamoyl)methyl methyl (2E)but-2-ene-1,4-dioate is selected from crystalline form 2, crystalline form 3 and crystalline form 4;
   crystalline form 2 exhibits characteristic scattering angles (2θ) at least at 8.4±0.2°, 4.2±0.2°, 16.9±0.2°, 18.3±0.2°, and 20.0±0.2° in an X-ray powder diffraction pattern measured using Cu—Kα radiation;
   crystalline form 3 exhibits characteristic scattering angle (2θ) at least at 20.6±0.2°, 9.5±0.2°, 11.1±0.2°, 15.8±0.2° and 18.6±0.2° in an X-ray powder diffraction pattern measured using Cu—Kα radiation; and
   crystalline form 4 exhibits characteristic scattering angle (2θ) at least at 20.4±0.2°, 8.2±0.2°, 8.2±0.2°, 26.3±0.2°, and 20.8±0.2° in an X-ray powder diffraction pattern measured using Cu—Kα radiation.

* * * * *